US011285101B2

(12) United States Patent
Alteheld et al.

(10) Patent No.: US 11,285,101 B2
(45) Date of Patent: Mar. 29, 2022

(54) SOFT CHEWABLE PHARMACEUTICAL PRODUCTS

(71) Applicant: Intervet Inc., Madison, NJ (US)

(72) Inventors: Susi Alteheld, Bad Kreuznach (DE); Stefan Fuchs, Essenheim (DE); Carina Hang, Grolsheim (DE); Jürgen Lutz, Wiesbaden (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/296,490

(22) Filed: Mar. 8, 2019

(65) Prior Publication Data

US 2019/0201332 A1 Jul. 4, 2019

Related U.S. Application Data

(63) Continuation of application No. 15/613,848, filed on Jun. 5, 2017, now abandoned, which is a continuation of application No. 14/390,040, filed as application No. PCT/EP2013/056987 on Apr. 3, 2013, now abandoned.

(Continued)

(30) Foreign Application Priority Data

Apr. 4, 2012 (EP) .................................. 121631980

(51) Int. Cl.
| | |
|---|---|
| *A61K 9/00* | (2006.01) |
| *A61K 31/42* | (2006.01) |
| *A61K 47/16* | (2006.01) |
| *A61K 47/22* | (2006.01) |
| *A61K 47/38* | (2006.01) |
| *A61K 31/422* | (2006.01) |
| *A61K 31/35* | (2006.01) |
| *A61K 31/7048* | (2006.01) |
| *A61K 47/42* | (2017.01) |
| *A61K 45/06* | (2006.01) |
| *A61K 47/12* | (2006.01) |
| *A61K 47/18* | (2017.01) |
| *A61K 47/36* | (2006.01) |
| *A61K 47/44* | (2017.01) |
| *A61K 47/20* | (2006.01) |
| *A61K 47/26* | (2006.01) |
| *A61K 47/10* | (2017.01) |
| *A61K 31/365* | (2006.01) |
| *A61K 9/20* | (2006.01) |
| *A61K 9/51* | (2006.01) |
| *A61K 9/50* | (2006.01) |
| *A61K 9/48* | (2006.01) |
| *A61K 9/28* | (2006.01) |
| *A61K 9/16* | (2006.01) |
| *A61K 9/14* | (2006.01) |
| *B29C 37/00* | (2006.01) |
| *B29C 43/00* | (2006.01) |
| *A61P 43/00* | (2006.01) |
| *A61P 33/14* | (2006.01) |
| *A61P 33/00* | (2006.01) |

(52) U.S. Cl.
CPC ............ *A61K 9/0056* (2013.01); *A61K 9/145* (2013.01); *A61K 9/1617* (2013.01); *A61K 9/2013* (2013.01); *A61K 9/282* (2013.01); *A61K 9/4858* (2013.01); *A61K 9/5015* (2013.01); *A61K 9/5123* (2013.01); *A61K 31/35* (2013.01); *A61K 31/365* (2013.01); *A61K 31/42* (2013.01); *A61K 31/422* (2013.01); *A61K 31/7048* (2013.01); *A61K 45/06* (2013.01); *A61K 47/10* (2013.01); *A61K 47/12* (2013.01); *A61K 47/16* (2013.01); *A61K 47/18* (2013.01); *A61K 47/20* (2013.01); *A61K 47/22* (2013.01); *A61K 47/26* (2013.01); *A61K 47/36* (2013.01); *A61K 47/38* (2013.01); *A61K 47/42* (2013.01); *A61K 47/44* (2013.01); *A61P 33/00* (2018.01); *A61P 33/14* (2018.01); *A61P 43/00* (2018.01)

(58) Field of Classification Search
CPC .... A61K 31/35; A61K 31/7048; A61K 47/42; A61K 45/06; A61K 47/12; A61K 47/18; A61K 47/36; A61K 47/44; A61K 47/20; A61K 47/26; A61K 47/10; A61K 31/365; A61K 9/20; A61K 9/51; A61K 9/50; A61K 9/48; A61K 9/28; A61K 9/16; A61K 9/14
See application file for complete search history.

(56) References Cited

U.S. PATENT DOCUMENTS 3,486,186 A 12/1969 Richards et al.
3,887,964 A 6/1975 Richards
(Continued)

FOREIGN PATENT DOCUMENTS

AU 2010206029 B2 8/2012
CN 1930136 3/2007
(Continued)

OTHER PUBLICATIONS

Office Action dated Jun. 7, 2016 for U.S. Appl. No. 14/390,040, 18 pages.
(Continued)

*Primary Examiner* — Dennis Heyer
(74) *Attorney, Agent, or Firm* — David J. Kerwick

(57) ABSTRACT

A soft chewable pharmaceutical product for delivery of a pharmaceutically acceptable active ingredient to an animal comprising pamoic acid or a pharmaceutically acceptable salt and a process for the manufacture of such soft chewable pharmaceutical product.

26 Claims, No Drawings

Related U.S. Application Data

(60) Provisional application No. 61/782,434, filed on Mar. 14, 2013.

(56) References Cited

U.S. PATENT DOCUMENTS

| | | | |
|---|---|---|---|
| 3,952,478 | A | 4/1976 | Richards et al. |
| 4,054,967 | A | 10/1977 | Sandberg et al. |
| 4,097,961 | A | 7/1978 | Richards |
| 4,182,003 | A | 1/1980 | Lamartino et al. |
| 4,284,652 | A | 8/1981 | Christensen |
| 4,327,076 | A | 4/1982 | Puglia et al. |
| 4,334,339 | A | 6/1982 | Holly |
| 4,338,702 | A | 7/1982 | Holly |
| 4,343,068 | A | 8/1982 | Holly |
| 4,356,595 | A | 11/1982 | Sandberg et al. |
| 4,372,008 | A | 2/1983 | Sandberg |
| 4,393,085 | A | 7/1983 | Spradlin et al. |
| 4,535,505 | A | 8/1985 | Holly et al. |
| 4,597,135 | A | 7/1986 | Holly et al. |
| 4,608,731 | A | 9/1986 | Holly |
| 4,609,543 | A | 9/1986 | Morris et al. |
| 4,622,717 | A | 11/1986 | Bollinger |
| 4,697,308 | A | 10/1987 | Sandberg |
| 4,768,941 | A | 9/1988 | Wagner |
| 4,780,931 | A | 11/1988 | Powers et al. |
| 4,818,446 | A | 4/1989 | Schreiber et al. |
| 4,821,376 | A | 4/1989 | Sandberg |
| 4,872,241 | A | 10/1989 | Lindee |
| 4,935,243 | A | 6/1990 | Borkan et al. |
| 4,975,039 | A | 12/1990 | Dare et al. |
| 4,996,743 | A | 3/1991 | Janssen |
| 4,997,671 | A | 3/1991 | Spanier |
| 5,021,025 | A | 6/1991 | Wagner |
| 5,022,888 | A | 6/1991 | Lindee |
| 5,236,730 | A | 8/1993 | Yamada et al. |
| 5,262,167 | A | 11/1993 | Vegesna et al. |
| 5,380,535 | A | 1/1995 | Geyer et al. |
| 5,439,924 | A | 8/1995 | Miller et al. |
| 5,578,336 | A | 11/1996 | Monte |
| 5,637,313 | A | 6/1997 | Chau et al. |
| 5,655,436 | A | 8/1997 | Soper |
| 5,753,255 | A | 5/1998 | Chavkin et al. |
| 5,824,336 | A | 10/1998 | Jans et al. |
| 5,827,565 | A | 10/1998 | Axelrod |
| 5,958,445 | A | 9/1999 | Humber et al. |
| 5,980,228 | A | 11/1999 | Soper |
| 6,060,078 | A | 5/2000 | Lee |
| 6,086,940 | A | 7/2000 | Axelrod |
| 6,093,427 | A | 7/2000 | Axelrod |
| 6,093,441 | A | 7/2000 | Axelrod |
| 6,110,521 | A | 8/2000 | Axelrod |
| 6,159,516 | A | 12/2000 | Axelrod et al. |
| 6,270,790 | B1 | 8/2001 | Robinson et al. |
| 6,387,381 | B2 | 5/2002 | Christensen |
| 6,500,463 | B1 | 12/2002 | van Lengerich |
| 7,348,027 | B2 | 3/2008 | Rose et al. |
| 7,662,972 | B2 | 2/2010 | Mita et al. |
| 7,947,715 | B2 | 5/2011 | Mita et al. |
| 7,951,828 | B1 | 5/2011 | Mita et al. |
| 7,955,632 | B2 | 6/2011 | Paulsen et al. |
| 8,022,089 | B2 | 9/2011 | Mita et al. |
| 8,138,213 | B2 | 3/2012 | Mita et al. |
| 8,426,460 | B2 | 4/2013 | Meng |
| 8,492,311 | B2 | 7/2013 | Mita et al. |
| 8,796,464 | B2 | 8/2014 | Moriyama et al. |
| 9,259,417 | B2 | 2/2016 | Soll et al. |
| 2001/0036464 | A1 | 11/2001 | Christensen |
| 2001/0055598 | A1 | 12/2001 | Kalbe et al. |
| 2003/0007958 | A1 | 1/2003 | Chen |
| 2004/0037869 | A1 | 2/2004 | Cleverly et al. |
| 2004/0043925 | A1 | 3/2004 | Kalbe et al. |
| 2004/0234579 | A1 | 11/2004 | Finke |
| 2005/0032718 | A1 | 2/2005 | Burke et al. |
| 2005/0226908 | A1 | 10/2005 | Huron et al. |
| 2006/0141009 | A1 | 6/2006 | Huron et al. |
| 2006/0222684 | A1 | 10/2006 | Isele |
| 2006/0228399 | A1 | 10/2006 | Rose et al. |
| 2007/0066617 | A1 | 3/2007 | Mita et al. |
| 2008/0075759 | A1* | 3/2008 | Paulsen .............. A61K 9/0056 424/439 |
| 2008/0293645 | A1 | 11/2008 | Schneider |
| 2009/0280159 | A1 | 11/2009 | Paulsen et al. |
| 2009/0281059 | A1 | 11/2009 | Falotico et al. |
| 2010/0144797 | A1 | 6/2010 | Mita et al. |
| 2010/0144808 | A1 | 6/2010 | Mita et al. |
| 2010/0144859 | A1 | 6/2010 | Meng |
| 2010/0173948 | A1* | 7/2010 | Lahm .................. A61K 31/42 514/340 |
| 2010/0179194 | A1 | 7/2010 | Mihara et al. |
| 2010/0179195 | A1 | 7/2010 | Lahm et al. |
| 2010/0249191 | A1 | 9/2010 | Coqueron et al. |
| 2010/0254960 | A1 | 10/2010 | Long et al. |
| 2011/0009438 | A1 | 1/2011 | Mita et al. |
| 2011/0059988 | A1 | 3/2011 | Heckeroth |
| 2011/0118212 | A1 | 5/2011 | Koerber et al. |
| 2011/0152312 | A1 | 6/2011 | Le Hir de Fallois et al. |
| 2011/0159107 | A1 | 6/2011 | Koerber et al. |
| 2011/0166193 | A1 | 7/2011 | Renold et al. |
| 2011/0223234 | A1 | 9/2011 | Paulsen et al. |
| 2011/0257011 | A1 | 10/2011 | Kaiser et al. |
| 2012/0030841 | A1 | 2/2012 | Koerber et al. |
| 2012/0035122 | A1 | 2/2012 | Vaillancourt et al. |
| 2012/0077765 | A1 | 3/2012 | Curtis et al. |
| 2013/0065846 | A1 | 3/2013 | Soll et al. |
| 2014/0141055 | A1 | 5/2014 | Kluger et al. |
| 2015/0057239 | A1 | 2/2015 | Freehauf et al. |
| 2017/0065565 | A1 | 3/2017 | Mita et al. |

FOREIGN PATENT DOCUMENTS

| | | |
|---|---|---|
| CN | 101190223 | 6/2008 |
| CN | 101743000 | 6/2010 |
| CN | 101765592 | 6/2010 |
| CN | 101778566 A | 7/2010 |
| CN | 101919857 | 12/2010 |
| CN | 101919857 A | 12/2010 |
| CN | 102088857 A | 6/2011 |
| CN | 102256971 | 11/2011 |
| CN | 101522672 B | 7/2012 |
| CN | 101909605 B | 7/2013 |
| CN | 101652354 B | 6/2014 |
| CN | 102088856 B | 11/2015 |
| EP | 0075443 A2 | 3/1983 |
| EP | 0273001 A2 | 6/1988 |
| EP | 0492235 A1 | 7/1992 |
| EP | 1023841 A1 | 8/2000 |
| EP | 1247456 A2 | 10/2002 |
| EP | 1688149 A1 | 8/2006 |
| EP | 1731512 A1 | 12/2006 |
| GB | 819681 | 9/1959 |
| GB | 2300103 A | 10/1996 |
| NZ | 286545 A | 11/1998 |
| WO | 1994025460 | 11/1994 |
| WO | 1999048372 A1 | 9/1999 |
| WO | 2001037667 A1 | 5/2001 |
| WO | 0200603 A1 | 3/2002 |
| WO | 2002060255 A2 | 8/2002 |
| WO | 2002094288 A1 | 11/2002 |
| WO | 2003030653 A2 | 4/2003 |
| WO | 2004014143 A1 | 2/2004 |
| WO | 2004017970 | 3/2004 |
| WO | 2005013714 A1 | 2/2005 |
| WO | 2005016261 | 2/2005 |
| WO | 2005016356 A1 | 2/2005 |
| WO | 2005062782 A2 | 7/2005 |
| WO | 2005075454 | 8/2005 |
| WO | 2005085216 | 9/2005 |
| WO | 2005099453 A1 | 10/2005 |
| WO | 2005099692 A1 | 10/2005 |
| WO | 2006005578 A2 | 1/2006 |
| WO | 2007067582 A2 | 6/2007 |
| WO | 2007070606 A2 | 6/2007 |
| WO | 2007075459 A2 | 7/2007 |
| WO | 2007079162 | 7/2007 |

(56) References Cited

FOREIGN PATENT DOCUMENTS

| | | | |
|---|---|---|---|
| WO | 2007123855 | A2 | 11/2007 |
| WO | 2008030469 | A2 | 3/2008 |
| WO | 2008134819 | A1 | 11/2008 |
| WO | 2008136791 | A1 | 11/2008 |
| WO | 2008144275 | A1 | 11/2008 |
| WO | 2008148027 | A1 | 12/2008 |
| WO | 2008154528 | A2 | 12/2008 |
| WO | 2009002809 | | 12/2008 |
| WO | 2009003075 | A1 | 12/2008 |
| WO | 2009024541 | A2 | 2/2009 |
| WO | 2009064859 | A1 | 5/2009 |
| WO | 2009080250 | | 7/2009 |
| WO | 2010003923 | A1 | 1/2010 |
| WO | 2010056999 | A1 | 5/2010 |
| WO | 2010070068 | | 6/2010 |
| WO | 2010079077 | | 7/2010 |
| WO | 2010084067 | A2 | 7/2010 |
| WO | 2011011235 | | 1/2011 |
| WO | 2011067272 | A1 | 6/2011 |
| WO | 2011075591 | A1 | 6/2011 |
| WO | 2011092287 | A1 | 8/2011 |
| WO | 2011104087 | A1 | 9/2011 |
| WO | 2011124998 | A1 | 10/2011 |
| WO | WO 2012/049156 | * | 10/2011 |
| WO | 2011149749 | A1 | 12/2011 |
| WO | 2011154433 | A2 | 12/2011 |
| WO | 2011154434 | A2 | 12/2011 |
| WO | 2011154494 | A2 | 12/2011 |
| WO | 2011157733 | A2 | 12/2011 |
| WO | 2012003231 | A1 | 1/2012 |
| WO | 2012007426 | A1 | 1/2012 |
| WO | 2012038851 | A1 | 3/2012 |
| WO | 2012049156 | A1 | 4/2012 |
| WO | 2013039948 | A1 | 3/2013 |
| WO | 2014079825 | A1 | 5/2014 |

OTHER PUBLICATIONS

Opposition Notice in the name of Ceva Sante Animale against patent EP2833866 in the name of Intervet International B.V. dated Aug. 27, 2019, 19 pages.
Opposition Notice in the name of Virbac against patent EP2833866 in the name of Intervet International B.V. dated Aug. 26, 2019, 30 pages.
Ozoe, et al., The antiparasitic isoxazoline A1443 is a potent blocker of insect ligand-gated chloride channels, Biochemical and Biophysical Research Communications, 2010, pp. 744-749, vol. 391.
Remington: The Science and Practice of Pharmacy, 20th edition, Pyrantel Pamoate, p. 1564, 2000, 3 pages.
Response to Office Action for U.S. Appl. No. 14/390,040, dated Sep. 29, 2016, 12 pages.
Translation of the opposition in the name of Ceva Sante Animale against patent EP2833866 in the name of Intervet International B.V. dated 2019, 22 pages.
Translation of the opposition in the name of Virbac against patent EP2833866 in the name of Intervet International B.V. dated 2019, 33 pages.
Clark, JN et al., Efficacy of ivermectin and pyrantel pamoate combined in a chewable formulation against heartworm, hookworm, and ascarid infections in dogs, Am J Vet Res, 1992, pp. 517-520, 53 (4).
Clark, JN et al., Evaluation of a beef-based chewable formulation of pyrantel pamoate against induced and natural infections of hookworms and ascarids in dogs, Veterinary Parasitology, 1991, pp. 127-133, 40.
Committee for Veterinary Medicinal Products, "Polyethylene Glycol Stearates and Polyethylene Glycol 15 Hydroxystearate",EMEA/MRL/392/98-FINAL-REV.1, 2003.
Declaration -Bd.R. 203(b), Interference 106,900, U.S. Appl. No. 15/634,924, dated Dec. 26, 2017, 8 pages.
European Search Report for 12163198.0, dated Aug. 16, 2012.
Gates, MC, et al., Factors influencing heartworm, flea, and tick preventive use in patients presenting to a veterinary teaching hospital, Preventive Veterinary Medicine, 2010, pp. 1-16, 93(2-3).
Nieubig, RR, Mind Your Salts: When the Inactive Constituent Isn't, Molecular Pharmacology, Jul. 22, 2010, pp. 558-559, vol. 78, No. 4,, EP.
PCT International Search Report for corresponding PCT/EP2013/056987, dated Aug. 12, 2013, 5 Pages.
PharmTech.com, Advancing Development and Manufacturing, "Salt Selection in Drug Development", vol. 32, Issue 3, Mar. 2, 2008, 13 pages.
Plumb, DC, Pyrantel pamoate, Veterinary Drug Handbook, 2011, pp. 880-882, 7th Edition.
Second Declaration of James E. Polli, Ph.D., Exhibit 2060, Interference 106,900, U.S. Appl. 15/634,924, filed Jun. 26, 2018, 70 pages.
Stahl, Ph et al., Pamoic Acid, Handbook of Pharmaceutical Salts, 2008, p. 301 (3 pages total).
Yu, X et al., The effectiveness of two anthelmintics vermox (mebendazole) and povan (pyrvinium pamoate), on thelastomatid nematodes (nematoda: oxyuroidea) of the cockroach, gromphadorhina portentosa, Ohio Journal of Science, 1990, pp. 152-155, 90 (5).
Aljaberi, Ahmad et al., Understanding and optimizing the dual excipient functionality of sodium lauryl sulfate in tablet formulation of poorly water soluble drug: wetting and lubrication, Pharmaceutical Development and Technology, 2013, 490-503, 18(2).
Beugnet, Frederic et al., Comparative efficacy of two oral treatments for dogs containing either afoxolaner or fluralaner against Rhipicephalus sanguineus sensu lato and Dermacentor reticulatus, Veterinary Parasitology, 2015, 142-145, 209.
Beugnet, Frederic et al., Comparative speed of efficacy against Ctenocephalides fells oftwo oral treatments for dogs containing either afoxolaner orfluralaner, Veterinary Parasitology, 2015, 297-301, 207.
Beugnet, Frédéric et al., Parasites of domestic owned cats in Europe: co-infestations and risk factors, Parasites & Vectors, 2014, 1-13, 7:291.
Colorcon Company, Starch 1500 Partially Pregelatinized Maise Starch, Technical Information Brochure, 2008, 1-6, Brochure.
Drug Bank, Pryantel, 2015, (updated Aug. 10, 2020) Accession No. DB11156, pp. 1-22.
European Medicines Agency EPAR Product Information for Bravecto, published 26, 2014, 20 pages.
European Medicines Agency, Science Medicines Health, CVMP assessment report for Bravecto, Committee for Medicinal Products for Veterinary Use (CVMP), 2013, 22 pages, N/A.
Intervet, Inc., Corrected Freedom of Informatioan Summary, NADA 141-426, 2014, 1-40, N/A.
Kilp, S et al., Pharmacokinetics of fluralaner in dogs following a single oral or intravenous administration, Parasites & Vectors, 2014, 1-5, 7:85.
Meadows, Cheyney et al., A randomized, blinded, controlled USA field study to assess the use of fluralaner tablets in controlling canine flea infestations, Parasites & Vectors, 2014, 1-8, 7:375.
Plerion 10 Packaging and Package Leaflet, Intervet UK Ltd. & Intervet Ireland Ltd. (2009). 6 pages.
Plerion 5 Packaging and Package Leaflet, Intervet UK Ltd. & Intervet Ireland Ltd. (2009), 4 pages.
Rohdich, N et al., A randomized, blinded, controlled and multi-centered field study comparing the efficacy and safety of Bravecto™ (fluralaner) against Frontline™ (fipronil) in flea- and tick-infested dogs, Parasites & Vectors, 2014, pp. 1-5, vol. 7, issue 83.
Summary of Product Characteristics, Plerion Chewable Tablets for Dogs from 2.5 kg, as published by Veterinary Medicines Directorate, UK (2014; initially authorized in 2009), 6 pages.
Summary of Product Characteristics, Plerion Chewable Tablets for Dogs from 5 kg, as published by Veterinary Medicines Directorate, UK (2014; initially authorized in 2009), 6 pages.
Taenzler, Janina, Onset of activity of fluralaner (BRAVECTO™) against Ctenocephalides felis on dogs, Parasites & Vectors, 2014, 1-4, 7:567.
Vercruysse, et al., Pharmacokinetics of Anthelmintics, 2014, pp. 1-4, MSD Manual-Veterinary Manual.

(56) References Cited

OTHER PUBLICATIONS

Walther, Felt M. et al., Safety of concurrent treatment of dogs with fluralaner (Bravecto™) and milbemycin oxime-praziquantel, Parasites & Vectors, 2014, 1-3, 7:481.
Walther, Felt M. et al., Safety of fluralaner chewable tablets (BravectoTM), a novel systemic antiparasitic drug, in dogs after oral administration, Parasites & Vectors, 2014, 1-7, 7:87.
Walther, Felt M. et al., Safety of fluralaner, a novel systemic antiparasitic drug, in MDR1(-/-) Collies after oral administration, Parasites & Vectors, 2014, 1-3, 7:86.
Walther, Felt M. et al., Safety of the concurrent treatment of dogs with Bravecto™ (fluralaner) and Scalibor™ protectorband (deltamethrin), Parasites & Vectors, 2014, 1-2, 7:105.
Walther, FM., et al., The effect of food on the pharmacokinetics, Parasites & Vectors, 2014, pp. 1-4, 7:84, Elsevier.
Wengenmayer, Christina et al., The speed of kill of fluralaner (Bravecto™) against Ixodes ricinus ticks on dogs, Parasites & Vectors, 2014, 1-5, 7:525.
Williams, Heike et al., Fluralaner, a novel isoxazoline, prevents flea (*Ctenocephalides fells*) reproduction in vitro and in a simulated home environment, Parasites & Vectors, 2014, 1-6, 7:275.
Remington: The Science and Practice of Pharmacy 20th Edition, 2000, p. 876.
Zhao ,et al, Targeting of the Orphan receptor GPR35 by Pamoic Acid, Molecular Pharmacology, 2010, pp. 560-568, vol. 78 ,No. 4.
National Office of Animal Health (NOAH), Compendium of Data Sheets for Animal Medicines, Plerion 5 and 10 Chewable Tablets for Dogs, 2010, 426-427, 582-583, 1098-1099 (5 pages).
CEVA, Opposition of EP 2833866, EPO Form 29110, dated Sep. 18, 2020.
CEVA, Opposition of EP 2833866, EPO Form 29110, translation of letter dated Sep. 10, 2020.
VIRBAC, Opposition of EP 2833866, EPO Form 29110, dated Sep. 10, 2020.
VIRBAC, Opposition of EP 2833866, EPO Form 29110, translation dated Sep. 10, 2020.
Al-Juhaimi, Fahad et al., Effects of different levels of Moringa (Moringa oleifera) seed flour on quality attributes of beef burgers, CyTA—Journal of Food, 2015, 1-11, N/A.
Brookfield Ametek, Texture Analysis Application Note: Cooked Hamburger Patties, Testing the Limited in texture analysis, 2019, 1-2, N/A.
Decision of Opposition Division against patent EP2833866 in the name of Intervet International B.V. dated Jul. 14, 2021, 30 pages.
Declaration of Brenda Valee Colon, in the matter of EP2833866, EP application No. 13715654.3, dated Sep. 4, 2020, 1 page.
Declaration Under 37 C.F.R. § 1.132 Of Keith Freehauf, U.S. Appl. No. 14/082,813, dated Jul. 26, 2016, 7 pages.
Declaration Under 37 C.F.R. § 1.132 Of Niki Waldron, U.S. Appl. No. 14/082,813, dated Dec. 17, 2015, 8 pages.
English language translation of letter from opponent 1 (Virbac) against patent EP2833866 in the name of Intervet International B.V. dated Mar. 26, 2021, 20 pages.
English language translation of letter from opponent 1 (Virbac) against patent EP2833866 in the name of Intervet International B.V. dated May 6, 2021, 14 pages.
English language translation of Letter from opponent 1 (Virbac) against patent EP2833866 in the name of Intervet International B.V. dated Sep. 10, 2020, 50 pages.
English language translation of letter from opponent 2 (CEVA) against patent EP2833866 in the name of Intervet International B.V. dated Sep. 10, 2020, 11 pages.
English translation of Evaluation of the influence of sodium pamoate on the preparation of compositions according to patent EP2833866, 9 pages.
Evaluation de l'influence du pamoate de sodium sur la preparation de compositions selon le brevet EP2833866, 8 pages.
Letter from opponent 1 (Virbac) against patent EP2833866 in the name of Intervet International B.V. dated Mar. 26, 2021, 13 pages.
Letter from opponent 1 (Virbac) against patent EP2833866 in the name of Intervet International B.V. dated May 6, 2021, 11 pages.
Letter from opponent 1 (Virbac) against patent EP2833866 in the name of Intervet International B.V. dated Sep. 10, 2020, 34 pages.
Letter from opponent 2 (CEVA) against patent EP2833866 in the name of Intervet International B.V. dated Sep. 10, 2020, 8 pages.
Opposition against European Patent EP 2833866 (Application No. 13715654.3), Intervet International BV, Reply to Summons for Oral Proceedings before the Opposition Division, dated Mar. 25, 2021, 92 pages.
Preliminary opinion of Opposition Division against patent EP2833866 in the name of Intervet International B.V. dated Feb. 11, 2020, 14 pages.
Reply to Notice of Opposition—a Summary Report—Processibility Assessment, 4 pages.
U.S. Appl. No. 61/728,379, filed Nov. 20, 2012, titled Manufacturing of Semi-Plastic Pharmaceutical Dosage Units, Number of p. 36.
Chinese Patent Application for Invention No. 201810385736.3, in the name of Intervet International B.V., reporting letter regarding Fourth Office Action, dated Dec. 10, 2021 (26 pages).
Sittig, Marshall et al., Pharmaceutical Manufacturing Encyclopedia, Changchun Publishing House, 1992, 771, N/A.

\* cited by examiner

SOFT CHEWABLE PHARMACEUTICAL PRODUCTS

CROSS-REFERENCE TO RELATED APPLICATIONS

This application is a Continuation of U.S. application Ser. No. 15/613,848, filed Jun. 5, 2017, which is a continuation of U.S. application Ser. No. 14/390,040, filed Oct. 2, 2014, which is the national stage entry under 35 U.S.C. § 371 of PCT/EP2013/056987, filed on Apr. 3, 2013, which claims priority to U.S. Provisional Application No. 61/782,434, filed on Mar. 14, 2013; and EP Application No. 12163198.0, filed on Apr. 4, 2012. The content of each of these applications is hereby incorporated by reference in its entirety.

FIELD OF THE INVENTION

The invention relates to the field of orally administrable pharmaceutical dosage units such as soft chews, especially for administration to non-human animals.

BACKGROUND OF THE INVENTION

Chewable pharmaceutical products for drug delivery are well known. Formulation of a drug into a chewable dosage form can increase (animal) patient acceptance of the medication that tend to resist swallowing hard tablets or capsules.

Texture is important for the acceptance of such oral products by (animal) patients. One of the most commonly used form for chewable pharmaceutical products is a chewable compressed tablet, whose ingredients, however, can make the tablet gritty or otherwise unappealing, especially to non-human animals. Thus, a preferred alternative dosage form for non-human animals is the "soft chew" generally a meat-like mass also widely found in consumable pet treats.

Soft chews have been described in prior art. U.S. Pat. No. 6,387,381 discloses an extrudate which is formed of a matrix having starch, sugar, fat, polyhydric alcohol and water. WO 2004/014143 relates to compositions and processes for the delivery of an additive to an organism in a form suitable for consumption, and in particular, in the form of a soft chew.

US 2009/0280159 and US 2011/0223234, relate to palatable edible soft chewable medication vehicles. The processes described herein relate to the problem that heat generated during the extrusion process causes deterioration in the stability of the active ingredient in the mixture.

Machines for the high volume production of molded food patties have been described to be useful for the manufacturing of soft chews for administration to non-human animals. Such machines are molding machines developed for use in producing molded food products, for example Formax F6™ molding machine made by the Formax Corporation or the molding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228.

Such machines are originally used to form hamburger patties from a supply of ground beef by forcing the ground beef under pressure into a multi-cavity mold plate which is rapidly shuttled on a linear slide between a fill position and a discharge position in which vertically reciprocable knockouts push the patties from the mold cavities.

For use in the manufacturing of soft chews, a dough mass is prepared with ingredients that lead to the meat-like texture of the resulting soft chew after forming and drying. For the manufacturing of a veterinary medicament on an industrial scale it is necessary to produce the soft chews by a forming machine that is able to produce high volume.

However, it has been observed that some soft chew components of the dough, that is fed to the forming equipment, cause the blocking of the movable parts, especially the mold plates in the forming machine. Accordingly, the art field is in search of soft chew compositions that are easily processable in forming equipment on an industrial scale.

Salts of pamoic acid are known as pamoates or embonates and are conventionally used as a counter ion of certain basic active ingredients to obtain long-acting pharmaceutical formulations.

Examples of pamoate salts of active ingredients in veterinary medicine are the anthelmintic compounds pyrantel pamoate and oxantel pamoate and the antihistamine hydroxycine pamoate. A number of active ingredients used in human health are pamoate salts, e.g. as disclosed in WO 94/25460, WO 05/016261, WO 04/017970, or WO 05/075454.

The use of pamoic acid or a pharmaceutically acceptable salt thereof as excipient in soft chew formulations has not been described.

It has now been found that the soft chews that comprise pamoic acid or a pharmaceutically acceptable salt thereof can be easily processed in a forming machine and that pamoic acid or a pharmaceutically acceptable salt thereof facilitates manufacturing of such soft chews on an industrial scale using a forming machine.

SUMMARY OF THE INVENTION

The invention provides a new soft chewable pharmaceutical product for administration to non-human animals and a process for its manufacture.

Accordingly, in one embodiment the present invention relates to a soft chewable veterinary pharmaceutical product (a "soft chew") comprising as ingredients,
- pamoic acid or a pharmaceutically acceptable salt thereof, provided that such pamoic acid or pharmaceutically acceptable salt thereof is not an active pharmaceutical ingredient,
- one or more active pharmaceutical ingredients,
- a liquid component,
- a forming agent, and
- optionally one or more excipients.

In one embodiment the invention provides a soft chewable veterinary pharmaceutical product comprising as ingredients,
- pamoic acid or a pharmaceutically acceptable salt thereof, provided that such pamoic acid or pharmaceutically acceptable salt thereof is not an active pharmaceutical ingredient,
- optionally one or more active pharmaceutical ingredients,
- a liquid component,
- a forming agent, and
- optionally one or more excipients.

In a preferred embodiment the product comprises sodium pamoate.

In one embodiment the amount of pamoic acid or the pharmaceutically acceptable salt thereof is between 1.5 and 30% w/w, preferably between 2 and 5% w/w.

In another embodiment a soft chewable veterinary pharmaceutical product is provided comprising as ingredients, a pamoate salt of an active pharmaceutical ingredient, provided that such active pharmaceutical ingredient is not pyrantel pamoate or oxantel pamoate,
optionally another active pharmaceutical ingredient,
a liquid component,
a forming agent,
optionally pamoic acid or a pharmaceutically acceptable salt thereof, and
optionally one or more excipients.

In one embodiment the product as described above additionally comprise one or more of the following excipients:
a filler,
a stabilizer component,
a flavoring component, and/or
a sugar component.

In one embodiment the active pharmaceutical ingredient is an isoxazoline compound of Formula (I)

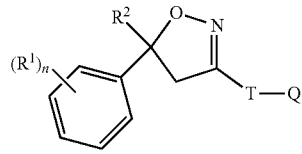

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain, especially a three or four membered chain;
Q=X—$NR^3R^4$ or a 5-membered N-heteroaryl ring, which is optionally substituted by one or more radicals;
X=$CH_2$, $CH(CH_3)$, CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

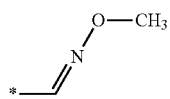 R³-1

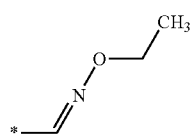 R³-2

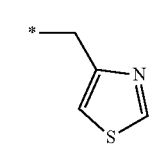 R³-3

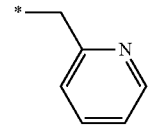 R³-4

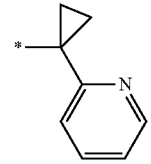 R³-5

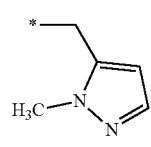 R³-6

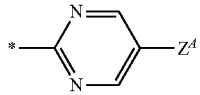 R³-7

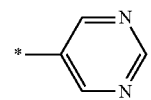 R³-8

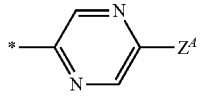 R³-9

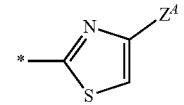 R³-10

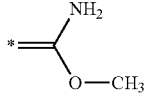 R³-11

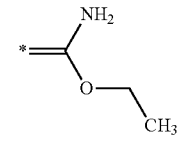 R³-12

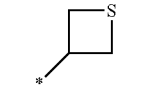 R³-13

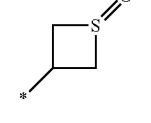 R³-14

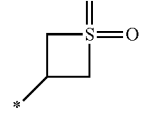 R³-15 wherein $Z^4$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

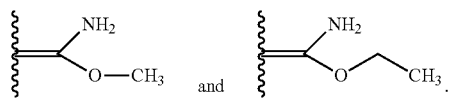

or a salt or solvate thereof.

In a specific embodiment the active pharmaceutical ingredient is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide.

In a specific embodiment the active pharmaceutical ingredient is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

In a specific embodiment the active pharmaceutical ingredient is 4-[5-(3,5-dichlorophenyl)-5-(trifluoromethyl)-4H-isoxazol-3-yl]-2-methyl-N-(thietan-3-yl)benzamide.

In a specific embodiment the active pharmaceutical ingredient is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide.

In one embodiment more than one active pharmaceutical ingredient is present.

In a preferred embodiment the combination of active pharmaceutical ingredients comprises one or more antiparasitics.

Another aspect of the current invention is a process for the manufacture of a product as described above in a forming machine comprising the steps of
 a) mixing the ingredients into a dough,
 b) filling a mold with dough, and
 c) removing the dough from the mold,
 wherein in the mixing step a) the pamoic acid or the pharmaceutically acceptable salt thereof is mixed with the other ingredients.

In one aspect the current invention is directed to the use of pamoic acid or a pharmaceutically acceptable salt thereof in the process as described above to increase lubricity of a product as described above when filling the mold with dough or when removing the dough from the mold or both.

In another aspect the current invention is directed to the use of the soft chewable veterinary pharmaceutical product as described above in the manufacture of a medicament for controlling a parasitic insect, acarid or nematode infestation of an animal.

Another aspect of the current invention is a soft chewable veterinary pharmaceutical composition comprising an isoxazoline compound of Formula (I) for use in a method of controlling a parasitic insect, acarid or nematode infestation of an animal

DETAILED DESCRIPTION OF THE INVENTION

The inventors identified, that the addition of pamoic acid or a pharmaceutically acceptable salt thereof to a soft chew dough, improves the processability of such soft chew in the forming equipment by increasing lubricity on the surface of the soft chew when filling the mold with dough or when removing the dough from the mold or both.

"Soft chew" or "Soft chewable veterinary pharmaceutical product" is intended to mean a product which is solid at room temperature and that is soft to chew and which is functionally chewy because the product has some plastic texture during the process of mastication in the mouth. Such soft chews have a softness that is similar to a cooked ground meat petty.

Pamoic acid, also called embonic acid, is a naphthoic acid derivative. The chemical name of pamoic acid is 4,4'-methylenebis(3-hydroxy-2-napthalenecarboxylic acid). In one aspect of the invention a salt of pamoic acid is used. In one aspect of the invention, the pharmaceutically acceptable salt of pamoic acid is the sodium or potassium salt. In one embodiment sodium pamoate is used, especially disodium pamoic acid. Salts of pamoic acid are readily commercially available, e.g. pamoic acid disodium salt from APAC Pharmaceutical LLC, Columbia, US. Different hydrate forms of pamoic acid salts are suitable for use in the current invention. In one embodiment the monohydrate form is used. In an alternative embodiment the anhydrate form is used. Alternatively esters of pamoic acid can be used in the current invention.

In one aspect the active pharmaceutical ingredient by itself does not provide a lubricating effect and pamoic acid or salts thereof are included in the soft chew composition as an (non-active) ingredient or excipient. Hence the composition comprises pamoic acid or salts thereof provided that such pamoic acid or pharmaceutically acceptable salt thereof is not an active pharmaceutical ingredient. In one example such pamoic acid or salts is sodium pamoate.

In addition to pamoic acid as a (non-active) ingredient (or excipient) the soft chew can comprise a pamoate salt of an active pharmaceutical ingredient.

In another aspect, the invention relates to a product of the invention wherein a pamoate salt of an active pharmaceutical ingredient is present in the soft chew of the current invention, but no additional pamoic acid or salts thereof are included as non-active ingredient, provided that such active pharmaceutical ingredient is not pyrantel pamoate or oxantel pamoate.

The presence of pamoic acid or a pharmaceutically acceptable salt thereof has been proven to increase the lubricity of the soft chew so that the soft chew can now be processed in a forming machine. The amount of pamoic acid or a pharmaceutically acceptable salt thereof necessary to provide the required lubricity depends on the specific composition of the various ingredients and can be determined by the skilled person in each case. In general, a w/w % of at least 1% already displays the favourable processing parameters of the soft chew.

In one aspect the invention relates to a product according to the invention wherein the amount of pamoic acid or the pharmaceutically acceptable salt thereof is between 1 and 50% w/w. In another aspect the amount of pamoic acid or the pharmaceutically acceptable salt thereof is between 1.5 and 30% w/w. In still another aspect the amount of pamoic acid or the pharmaceutically acceptable salt thereof is not higher than 10% w/w. In a further aspect, the amount of pamoic acid or the pharmaceutically acceptable salt thereof is between 2.0 and 5.0% w/w.

Another aspect of the present invention is the use of pamoic acid or a pharmaceutically acceptable salt thereof in the manufacture of a soft chew. The addition of pamoic acid, or a pharmaceutically acceptable salt thereof to a soft chew dough, improves the processability of such soft chew dough in the forming equipment by increasing lubricity on the surface of the soft chew product when filling the mold with dough or when removing the dough from the mold or both. Lubricity means and refers to the measure of the reduction in friction including reduction of adherence of soft-chew mixture to the mold plate or knock out cups.

In one embodiment the pamoic acid or pharmaceutically acceptable salt thereof is not an active pharmaceutical ingredient.

The soft chew according to the invention in general comprises an active pharmaceutical ingredient.

As used herein, an active pharmaceutical ingredient (or active ingredient, or pharmaceutically active ingredient or pharmaceutically acceptable active ingredient) is a substance used in a pharmaceutical product, intended to furnish pharmacological activity or to otherwise have direct effect in the diagnosis, cure, mitigation, treatment or prevention of disease, or to have direct effect in restoring, correcting or modifying physiological functions in humans or animals.

Any orally administrable pharmaceutically active ingredient or other biologically active compound may be provided in the soft chews of the invention. Those of ordinary skill in the veterinary pharmaceutical arts will be entirely familiar with the identity of such active ingredients which may include, without limitation, antibiotics, analgesics, antivirals, antifungals, antiparasitics such as endo- and ecto-parasticides, hormones and/or derivatives thereof, anti-inflammatories (including non-steroidal anti-inflammatories), steroids, behavior modifiers, vaccines, antacids, laxatives, anticonvulsants, sedatives, tranquilizers, antitussives, antihistamines, decongestants, expectorants, appetite stimulants and suppressants, cardiovascular drugs, minerals and vitamins.

The active ingredients are preferably antiparasitics, more preferably selected from the group consisting of isoxazoline compounds, avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidine (morantel and pyrantel), salicylanilides (e.g., closantel, oxyclozanide, rafoxanide, and niclosamide); nitrophenolic compounds (e.g., nitroxynil and nitroscanate); benzenedisulfo-namides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); amidine compounds (e.g., amidantel and tribendimidin), including all pharmaceutically acceptable forms, such as salts, solvates or N-oxides.

In one embodiment the pharmaceutically active ingredient is an isoxazoline compound. Isoxazoline compounds are known in the art and these compounds and their use as antiparasitics are described, for example, in US patent application US 2007/0066617, and International Patent applications WO 2005/085216, WO 2007/079162, WO 2009/002809, WO 2009/024541, WO 2009/003075, WO 2010/ 070068 and WO 2010/079077, the disclosures of which, as well as the references cited herein, are incorporated by reference. This class of compounds is known to possess excellent activity against ectoparasites, i.e. parasitic insect and acarids, such as ticks and fleas and endoparasites such as nematodes.

In one embodiment the soft chewable pharmaceutical product according to the invention comprises an isoxazoline compound of the Formula (I)

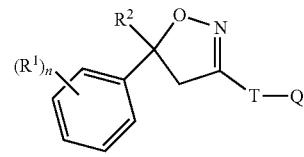

Formula (I), wherein $R^1$=halogen, $CF_3$, $OCF_3$, CN, n=integer from 0 to 3, preferably 1, 2 or 3, $R^2$=$C_1$-$C_3$-haloalkyl, preferably $CF_3$ or $CF_2Cl$, T=5- or 6-membered ring, which is optionally substituted by one or more radicals Y, Y=methyl, halomethyl, halogen, CN, $NO_2$, $NH_2$—C=S, or two adjacent radicals Y form together a chain CH—CH=CH—CH, N—CH=CH—CH, CH—N=CH—CH, CH—CH=N—CH, or CH—CH=CH—N, HC=HC—CH, CH—CH=CH, CH=CH—N, N—CH=CH;

Q=X—$NR^3R^4$ or a 5-membered N-heteroaryl ring, which is optionally substituted by one or more radicals $Z^A$, $Z^B$ $Z^D$;

X=$CH_2$, CH($CH_3$), CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

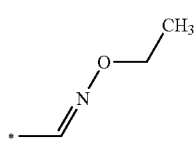

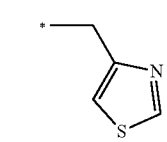

-continued

R³-4 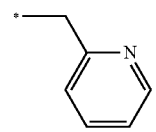

R³-5 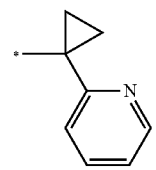

R³-6 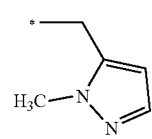

R³-7 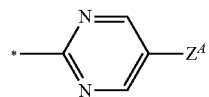

R³-8 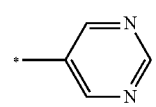

R³-9 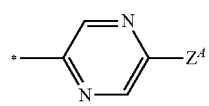

R³-10 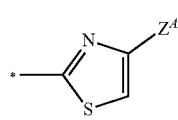

R³-11 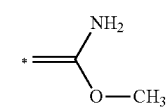

R³-12 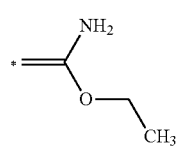

R³-13 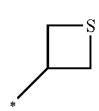

R³-14 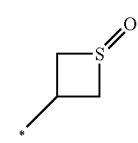

-continued

R³-15 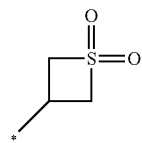

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or $R^3$ and $R^4$ together form a substituent selected from the group consisting of:

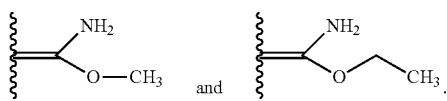

wherein $Z^A$=hydrogen, halogen, cyano, halomethyl ($CF_3$).

In one preferred embodiment in Formula (I) T is selected from

T-1 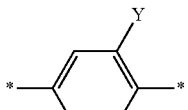

T-2 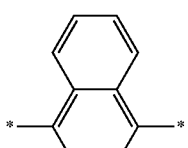

T-3 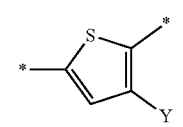

T-4 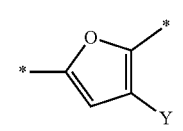

T-5 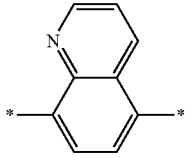

T-6 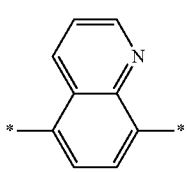

-continued
T-7
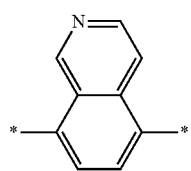
T-8
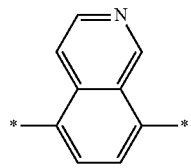
T-9
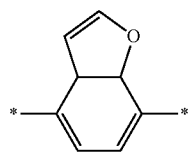
T-10
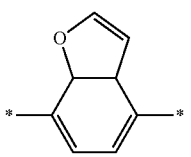
T-11
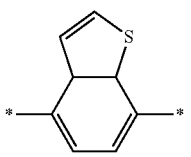
T-12
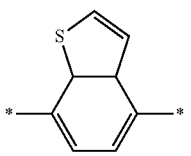
T-13
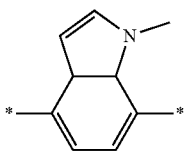
T-14
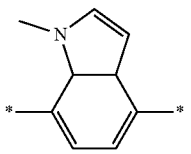
T-15
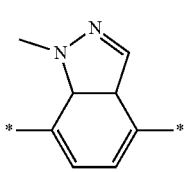
-continued
T-16
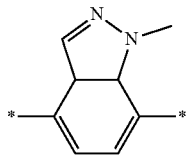
T-17
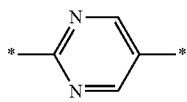
T-18
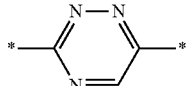
T-19
T-20
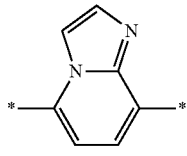
T-21
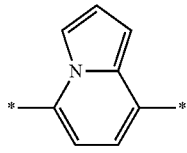
T-22
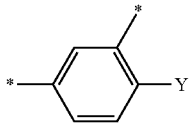
wherein in T-1, T-3 and T-4 the radical Y is hydrogen, halogen, methyl, halomethyl, ethyl, haloethyl.
In an preferred embodiment in Formula (I) Q is selected from
Q-1
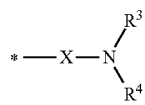
Q-2
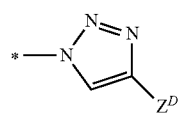
Q-3
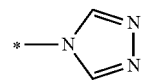
Q-4
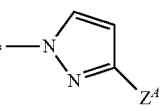

-continued
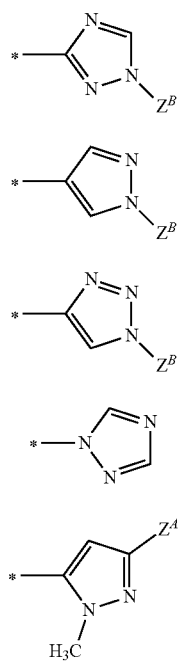
Q-5
Q-6
Q-7
Q-8
Q-9
Wherein R³, R⁴, X and Z^A are as defined above.
Z^B = 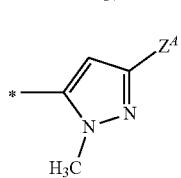  Z^B-1
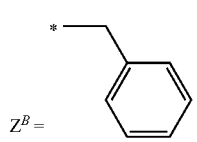  Z^B-2
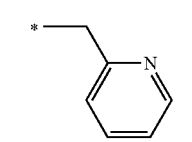  Z^B-3
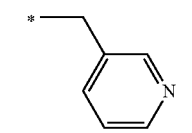  Z^B-4
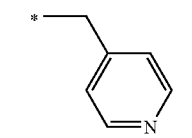  Z^B-5
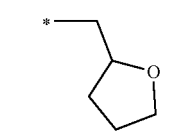  Z^B-6
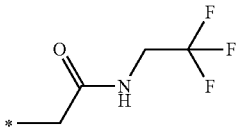  Z^B-7
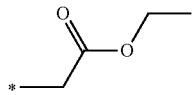  Z^B-8
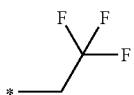  Z^B-9
Z^D = 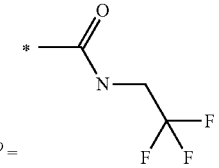  Z^D-1
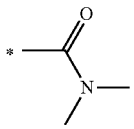  Z^D-2
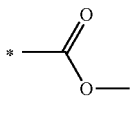  Z^D-3
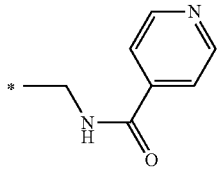  Z^D-4
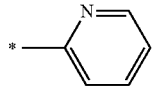  Z^D-5
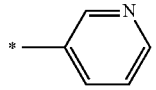  Z^D-6

Preferred compounds of Formula (I) are:

| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-Cl, 5Cl | CF₃ | CH₂C(O)NHCH₂CH₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-CF₃ | CF₃ | CH₂C(O)NHCH₂CH₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-CF₃, 5-Cl | CF₃ | CH₂C(O)NHCH₂CH₃ | H | T-2 | — | Q-1 | — | C(O) |
| 3-Cl, 5Cl | CF₃ | — | | T-2 | — | Q-6 | $Z^B$-7 | |
| 3-Cl, 5Cl | CF₃ | — | — | T-2 | — | Q-7 | $Z^B$-7 | |
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-Cl, 5Cl | CF₃ | CH₂C(O)NHCH₂CH₃ | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-CF₃, 5-CF₃ | CF₃ | CH₂C(O)NHCH₂CH₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CH₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CH₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-Cl, 5-Cl | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CH₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-CF₃, 5-CF₃ | CF₃ | CH₂C(O)NHCH₂CH₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂C(O)NHCH₂CH₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | CH₂C(O)NHCH₂CH₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

Especially preferred compounds of Formula (I) are

| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-Cl, 5Cl | CF₃ | — | | T-2 | — | Q-6 | $Z^B$-7 | |
| 3-Cl, 5Cl | CF₃ | — | — | T-2 | — | Q-7 | $Z^B$-7 | |
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |

-continued

| (R¹)ₙ | R² | R³ | R⁴ | T | Y | Q | Z | X |
|---|---|---|---|---|---|---|---|---|
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred compound has the Formula (II),

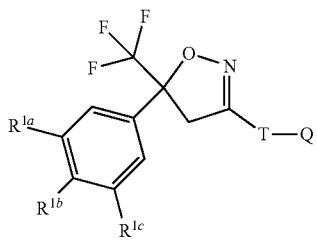

Formula II wherein $R^{1a}$, $R^{1b}$, $R^{1c}$ are independently from each other hydrogen, Cl or CF₃, preferably $R^{1a}$ and $R^{1c}$ are Cl or CF₃ and $R^{1b}$ is hydrogen, T is

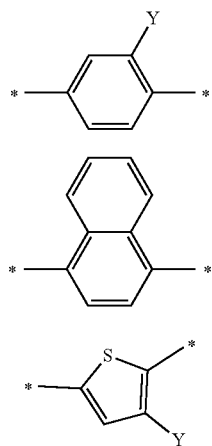

T-1

T-2

T-3

T-20

T-21

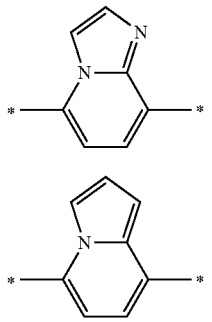

wherein Y is methyl, bromine, Cl, F, CN or C(S)NH₂, and Q is as described above.

In another preferred embodiment in R³ is H and R⁴ is —CH₂—C(O)—NH—CH₂—CF₃, —CH₂—C(O)—NH—CH₂—CH₃, —CH₂—CH₂—CF₃ or —CH₂—CF₃.

In one embodiment the compound of Formula (I) is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

In another embodiment the compound of Formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the compound of Formula (I) is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250—Compound B.

In another embodiment the compound of Formula (I) is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaner) that was disclosed in WO2007/079162—Compound C.

In another embodiment the compound of Formula (I) is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068—Compound D.

An especially preferred compound is (fluralaner-Compound A)

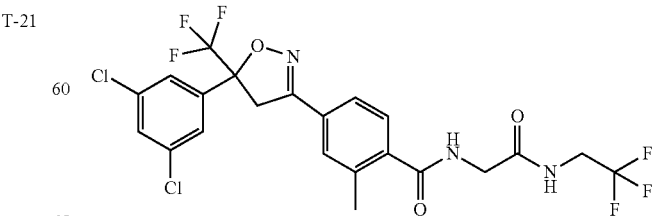

Especially preferred compounds of Formula (II) are:

| (R¹)ₙ | R² | R³ | R⁴ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

Isoxazoline compounds are known in the art and these compounds and their use as parasiticide aredescribed, for example, in US patent application No. US 2007/0066617, and International Patent applications WO 2007/079162, WO 2009/002809, WO 2009/024541, WO 2009/003075, WO2009/080250, WO 2010/070068, WO 2010/079077, WO 2011/075591 and WO 2011/124998, the disclosures of which, as well as the references cited herein, are incorporated by reference. This class of compounds is known to possess excellent activity against ectoparasites such as ticks and fleas.

The isoxazoline compounds may exist in various isomeric forms. A reference to an isoxazoline compound always includes all possible isomeric forms of such compound. Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Isoxazoline compounds of Formula (I) can be prepared according to one or other of the processes described e.g. in Patent Applications US 2007/0066617, WO 2007/079162, WO 2009/002809, WO 2009/080250, WO 2010/070068, WO 2010/079077, 2011/075591 and WO 2011/124998 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

In one embodiment the isoxazoline compound is 4-[5-(3, 5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN [864731-61-3])—USAN furalaner—Compound A.

This invention is also directed to soft chews with combinations comprising more than one pharmaceutically active ingredient. Preferred combinations comprising active ingredients selected from the group consisting of isoxazolines of Formula (I) and avermectins and milbemycins. In one embodiment the soft chew comprises a combination of isoxazolines, especially fluralaner—compound A, or afoxolaner with ivermectin. In another embodiment the soft chew comprises a combination of isoxazolines, especially fluralaner—compound A, or afoxolaner with milbemycin or moxidectin.

Other combinations of the present invention can include insect or acarid growth regulators (AGRs or IGRs) such as e.g. fenoxycarb, lufenuron, diflubenzuron, novaluron, triflumuron, fluazuron, cyromazine, methoprene, pyriproxyfen etc., thereby providing both initial and sustained control of parasites (at all stages of insect development, including eggs) on the animal subject, as well as within the environment of the animal subject.

The amounts of each of the components in the final product may be varied considerably, depending upon the nature of the pharmaceutically active ingredients, the weight and condition of the subject treated, and the unit dosage desired. Those of ordinary skill in the art will be able to adjust dosage amounts for particular pharmaceutically active ingredients in the soft chews in light of the teachings of this disclosure.

Generally, however, the pharmaceutically active ingredients may be provided by range in weight based on the total weight of the composition from about 0.001% to 75% (w/w), more preferably 0.1% to 40%, and most preferably not in excess of 50%.

For example, for administration for the control of ectoparasites in dogs, such as Compound A for treatment of fleas and ticks (see, Example 1) the amount of Compound A in the product of the invention is between 5% and 20% w/w, especially about 9% w/w or about 14% w/w.

The soft chew according to the invention comprises as (non-active) ingredient a liquid component. As used herein the liquid component includes aqueous and non-aqueous solvents, oils or humectant components or mixtures of any of such liquids. In one embodiment the liquid component is oil or a mixture of oils. In another embodiment the liquid component comprises one or more oils and one or more non-aqueous solvents. In one embodiment the liquid component comprises one or more oils, one or more non-aqueous solvents and a humectant.

The oil employed in the soft chew may be a saturated or unsaturated liquid fatty acid, its glyceride derivatives or fatty acid derivatives of plant or animal origin or a mixture thereof.

Suitable sources for vegetable fats or oils can be palm oil, corn oil, castor oil, canola oil safflower oil, cotton-seed oil, soybean oil, olive oil, peanut oil and mixtures thereof. Additionally, animal oil or fats and a mixture of animal or vegetable oils or fats are suitable for use in the product according to the invention. Vegetable oils may also be utilized to lubricate the soft chew mixture and maintain its softness. In one embodiment the oily component is soybean oil.

As used herein, the term "non-aqueous solvent" is intended to mean any liquid other than water in which a biological material may be dissolved or suspended and includes both inorganic solvents and, more preferably, organic solvents.

Illustrative examples of suitable non-aqueous solvents include, but are not limited to, the following: acetone, acetonitrile, benzyl alcohol, butyl diglycol, dimethylacetamide (DMA), dimethylsulfoxide (DMSO), dimethylformamide, N,N-diethyl-3-methylbenzamide, dipropylene glycol n-butyl ether, ethyl alcohol, isopropanol, methanol, butanol, phenylethyl alcohol, isopropanol, ethylene glycol monoethyl ether, ethylene glycol monomethyl ether, monomethylaceamide, dipropylene glycol monomethyl ether, liquid polyoxyethylene glycols, propylene glycol, N-methylpyrrolidone (NMP), 2-pyrrolidone, limonene, eucalyptol, dipropylene glycol monomethyl ether, diethylene glycol monoethyl ether, ethylene glycol, diethyl phthalate, polyethoxylated castor oil, methyl ethyl ketone, ethyl-L-lactate, lactic acid, fructone, glycerol formal, ethyl acetate, 1-methoxy-2-propyl acetate, ethyl acetoacetate, geranyl acetate, benzyl benzoate, propylene carbonate, methyl salicylate, isopropyl myristate, isopropylidene glycerol, propylene glycol methyl ether, diethylene glycol monoethyl ether, γ-hexalactone. In one embodiment the non-aqueous solvent is 2-pyrrolidone.

As used herein, the term "humectant" means and refers to a hygroscopic substance. It can be a molecule with several hydrophilic groups, e.g. hydroxyl groups, but amines and carboxyl groups, sometimes esterified, can be encountered as well; the affinity to form hydrogen bonds with molecules of water is crucial here.

The humectant has the effect of keeping the soft chew dough moist. Examples of humectants include propylene glycol, glyceryl triacetate, vinyl alcohol and neoagarobiose. Others can be sugar polyols such as glycerol, sorbitol, xylitol and maltitol, polymeric polyols like polydextrose, or natural extracts like quillaia, lactic acid, or urea. In one embodiment the humectant is glycerol.

In an embodiment, the liquid component comprises about 5% to about 50% w/w of the soft chew. In an alternate embodiment, a liquid component comprises about 7.5% to about 40 w/w of the soft chew. In an alternate embodiment, a liquid component comprises about 10% to about 30% w/w of the soft chew. In an alternate embodiment, a liquid component comprises about 15% to about 25% w/w of the soft chew.

The forming agent is important for the texture of the soft chew and the possibility to form single soft chews from the dough that stay intact and separate. As used herein, the term "former" or "forming agent" means and refers to an agent providing texture to the soft chew product, like for example polyethylene glycol (PEG) or polyvinylpyrrolidone (PVP).

In an embodiment, a forming agent of choice is polyethylene glycol (PEG). Moreover, depending upon the desired consistency of the soft chew, different molecular weight PEG may be utilized. In an embodiment, PEG 3350 is utilized. However, the PEG chosen is a matter of choice and the molecular weight may be higher or lower than 3350, but preferably higher than 600. Alternatively PEG 8000 might be used.

In an embodiment, the forming agent comprises about 1% to about 40% w/w of the soft chew. In an alternate embodiment, a forming agent comprises about 5% to about 30% w/w % of the soft chew. In an alternate embodiment, a forming agent comprises about 10% to about 20% w/w of the soft chew. In case the forming agent is polyvinylpyrrolidone e.g. 2, 4, 5, 6 or 9 w/w are present in the soft chew.

The product according to the current invention conventionally further comprise physiologically acceptable formulation excipients known in the art e.g. as described in "Gennaro, Remington: The Science and Practice of Pharmacy" (20th Edition, 2000) incorporated by reference herein. All such ingredients, carriers and excipients must be substantially pharmaceutically or veterinary pure and non-toxic in the amounts employed and must be compatible with the pharmaceutically active ingredients.

Additional excipients that can be present in the soft chew are e.g. a filler, a flavour, or sugar components.

As used herein, the term "filler" or "filler component" means and refers to those food-stuffs containing a preponderance of starch and/or starch-like material. Examples of filler are cereal grains and meals or flours obtained upon grinding cereal grains such as corn, oats, wheat, milo, barley, rice, and the various milling by-products of these cereal grains such as wheat feed flour, wheat middlings, mixed feed, wheat shorts, wheat red dog, oat, hominy feed, and other such material. Alternative non-food stuff fillers such as e.g. lactose may be used. In one embodiment the filler is starch, corn starch being preferred.

Flavours are commonly added to soft chewable pharmaceutical products to enhance their palatability. For example, a veterinary medication might include animal product-based flavourings such as beef, pork, chicken, turkey, fish and lamb, liver, milk, cheese and egg may be utilized.

Non-animal origin flavourings are plant proteins, such as soy protein, yeasts, or lactose to which edible artificial food-like flavourings has been added. Depending on the target animal, other non-animal flavourings could include anise oil, carob, peanuts, fruit flavours, herbs such as parsley, celery leaves, peppermint, spearmint, garlic, or combinations thereof.

The sugar component may act as a sweetener, filler or flavour or provides a texture that is appealing to the animal, e.g. crunchy texture. As used herein, the term "sugar component" and any conjugation thereof, means and refers to any saccharide which is at least partially soluble in moisture, non-toxic, and preferably not provide any undesirable taste effects. Further, the use of the term "sugar" shall include a "sugar substitute" or an "artificial sweetener". The sugar component may comprise white sugar, corn syrup, sorbitol, mannitol, oligosaccharide, isomalto oligosaccharide, fructose, lactose, glucose, lycasin, xylitol, lactitol, erythritol, mannitol, isomaltose, polydextrose, raffinose, dextrin, galactose, sucrose, invert sugar, honey, molasses, polyhydric alcohols and other similar saccharides oligomers and polymers and mixture thereof or artificial sweeteners such as saccharine, aspartame and other dipeptide sweeteners. In one embodiment the sweetener is aspartame.

Various embodiments further comprise additional excipients such as surfactants, stabilizer, flow agents, disintegration agents, preservatives and/or lubricating agents.

Surfactant components are well-known in the art. A suitable surfactant is e.g. sodium lauryl sulphate.

Suitable stabilizer components are citric acid, sodium citrate, and/or the like and antioxidants such as BHT, BHA, Ascorbic acid, Tocopherol, EDTA.

Flow agents typically may include silica dioxide, modified silica, fumed silica, talc and any other suitable material to assist bulk movement of active components and/or the combination during delivery and/or manufacture.

Disintegration agents typically may include sodium starch glycolate, pregelatinized corn starch (Starch 1500), crospovidone (Polyplasdone XL™, International Specialty Products), and croscarmellose sodium (Ac-Di-Sol™, FMC Corp.), and derivatives thereof and any other suitable material to help breakdown the dosage form and to assist in delivery of active ingredients.

Preservative for oral formulations are known in the art and are included in order to retard growth of microorganisms such as bacteria and fungi. An embodiment of preservative includes products such as potassium sorbate, sodium benzoate or calcium propionate.

Lubricating agents are e.g. magnesium stearate, fumaric acid, sodium stearyl fumarate.

Process of Manufacturing

Preferably, dry ingredients of the chew mixture are blended first; then the liquid components (e.g., oil, humectants or solvents) are added and blended therein to form a thoroughly blended mixture. After blending, the soft chew mixture is discharged from a port through the blender into a suitable container for processing into individual dosage units by hand or preferably with a forming machine.

A variety of forming equipment may be utilized in the invention, but those particularly preferred for use are molding machines developed for use in producing molded food products, such as pre-formed hamburger patties and chicken nuggets. For example, the molding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228 (the disclosures of which are incorporated herein) are representative of forming equipment that may be utilized in the invention.

Preferred forming equipment for use in the invention includes the Formax F6™ molding machine made by the Formax Corporation. The F6 machine has the capabilities of 60 strokes per minute. A square forming die of 6" by 6" can be used to form approximately 16-25 chunk-like soft chew units per stroke, each unit weighing 4 grams and being approximately ⅝" by ⅝" in size. Dies for production of other sizes or shapes (e.g., bone shaped chews) may also be utilized.

In such a machine, rotating screws and a plunger cause the chew mixture to move through a product tunnel to fill cavities in a mold plate. The mold plate is advanced from the filling position to the discharge position. There a knockout mechanism, with cups aligned with the cavities, ejects the molded mixture from all the mold plate cavities simultaneously. After discharge, the mold plate is retracted so the cycle can begin again.

Each batch of chews may be packaged in bulk or, preferably, each soft chew is then individually packaged for storage. Examples of suitable packaging materials include HDPE bottles, blister or foil/foil packaging.

Methods of Using the Soft Chews

In one embodiment the product of the invention is intended for use for controlling a parasitic insect- and acarid or helminth, especially parasitic nematode infestation. The term "controlling a parasitic insect- and acarid infestation" refers to preventing, reducing or eliminating an infestation by such parasites on animals preferably by killing the insects and/or acarids or nematode parasites within hours or days.

The term "parasitic insect- and acarid" refers to ectoparasites e.g. insect and acarine pests that commonly infest or infect animals. Examples of such ectoparasites include the egg, larval, pupal, nymphal and adult stages of lice, fleas, mosquitoes, mites, ticks biting or nuisance fly species. Especially important are the adult stages of fleas and ticks.

In general, the product according to the invention will contain an effective amount of the active ingredients, meaning a non-toxic but sufficient amount to provide the desired control effect. A person skilled in the art using routine experimentation may determine an appropriate "effective" amount in any individual case. Such an amount will depend on the age, condition, weight and type of the target animal. The soft chews may be formulated to contain an amount of active ingredients that is adjusted to animals in a specific weight range. The animals may receive a dosage every 2, 3, 4, 5 or 6 months or receives a monthly, weekly or daily dosage. The treatment can, for example, be continuing or seasonal.

In general the product according to the current invention can be administered to all species of animals that have insect—or acarid—or helminth parasite infestation. The recipient of the product may be a livestock animal, e.g. sheep, cattle, pig, goat or poultry; a laboratory test animal, e.g. guinea pig, rat or mouse; or a companion animal, e.g. dog, cat, rabbit, ferret or horse. The product according to the invention is especially suitable for use in companion animals, e.g. dogs, cats or ferrets.

As used herein, the term "w/w" designates weight/weight, the term "w/v" designates weight/volume, and the term "mg/kg" designates milligrams per kilogram of body weight. As used herein, % w/w represents the percentage by weight of an ingredient in the recipe of the product.

The invention having been fully described, its practice is illustrated by the examples provided below. The examples do not limit the scope of the invention, which is defined entirely by the appended claims.

Example 1

Soft Chew According to the Invention

Exemplary Method of Manufacture for Soft Chews of the Invention

Dry powdery ingredients which exhibited aggregates were sieved through an 800 μm screen. All dry powdery ingredients were weighed in and placed in the mixing vessel of a horizontal ploughshare or planetary mixing blender and mixed until the blend was visually practically homogeneous, i.e. approximately 10 minutes.

The defined amount of glycerol was added slowly followed by a short mixing. Oily components were added slowly followed again by a short mixing. If necessary, the mixer was heated to a temperature inhibiting a too fast precipitation of the PEG which introduced in the next step.

The PEG 3350 was molten. The defined amount of the molten PEG was added relatively quickly to the chew mixture, which was then mixed until the mixture was homogeneous and could be separated from the wall. The mixture resembled a "cookie dough-like" appearance.

The mixture was formed into individual chunks using a Formax F6™ molding machine with dies for production of chunk-like shapes, and packaged for storage.

Examples of soft chews according to the invention comprising 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide—Compound A as active ingredients are set forth below.

| Substance | mass [mg] | % |
|---|---|---|
| Formulation A | | |
| Active ingredient | 500.0 | 8.93 |
| Flavour | 1120.0 | 20.00 |
| Sucrose | 392.0 | 7.00 |
| Corn starch (filler) | 883.2 | 15.77 |
| Sodium lauryl sulfate | 112.0 | 2.00 |
| Sodium pamoate | 140.0 | 2.50 |
| Magnesium stearate | 42.0 | 0.75 |
| Aspartame | 14.0 | 0.25 |
| Glycerol | 420.0 | 7.50 |
| Soybean oil (0.1% BHT-stabilized) | 1024.8 | 18.30 |
| Polyethylene glycol 3350 | 952.0 | 17.00 |
| SUM | 5600.0 | 100.00 |
| Formulation B | | |
| Active ingredient | 500.00 | 8.93 |
| Flavor | 1120.00 | 20.00 |
| Sucrose | 392.00 | 7.00 |
| Corn starch (filler) | 1163.20 | 20.77 |
| Sodium lauryl sulfate | 112.00 | 2.00 |
| Sodium pamoate | 112.00 | 2.00 |
| Magnesium stearate | 42.00 | 0.75 |
| Aspartame | 14.00 | 0.25 |
| Glycerol | 420.00 | 7.50 |
| Soybean oil (0.1% BHT-stabilized) | 688.80 | 12.30 |
| Polyethylene glycol 3350 | 1036.00 | 18.50 |
| SUM | 5600.00 | 100.00 |
| Formulation C | | |
| Active ingredient | 500.00 | 8.93 |
| Flavor | 560.00 | 10.00 |
| Sucrose | 1148.00 | 20.50 |
| Corn starch (filler) | 1135.20 | 20.27 |
| Sodium lauryl sulfate | 112.00 | 2.00 |
| Sodium pamoate | 112.00 | 2.00 |
| Magnesium stearate | 42.00 | 0.75 |
| Aspartame | 14.00 | 0.25 |
| Glycerol | 224.00 | 4.00 |
| Soybean oil (0.1% BHT-stabilized) | 716.80 | 12.80 |
| Polyethylene glycol 3350 | 1036.00 | 18.50 |
| SUM | 5600.00 | 100.00 |
| Formulation D | | |
| Active ingredient | 500.00 | 8.93 |
| Flavor | 1120.00 | 20.00 |
| Sucrose | 392.00 | 7.00 |
| Corn starch (filler) | 1135.20 | 20.27 |
| Sodium lauryl sulfate | 112.00 | 2.00 |
| Sodium pamoate | 112.00 | 2.00 |
| Magnesium stearate | 42.00 | 0.75 |
| Aspartame | 14.00 | 0.25 |
| Glycerol | 420.00 | 7.50 |
| Soybean oil (0.1% BHT-stabilized) | 800.80 | 14.30 |
| Polyethylene glycol 3350 | 952.00 | 17.00 |
| SUM | 5600.00 | 100.00 |
| Formulation E | | |
| Active ingredient | 500.00 | 13.89 |
| Flavor | 720.00 | 20.00 |
| Sucrose | 252.00 | 7.00 |
| Corn starch (filler) | 569.20 | 15.81 |
| Sodium lauryl sulfate | 72.00 | 2.00 |
| Sodium pamoate | 72.00 | 2.00 |
| Magnesium stearate | 27.00 | 0.75 |
| Aspartame | 9.00 | 0.25 |
| Glycerol | 270.00 | 7.50 |
| Soybean oil (0.1% BHT-stabilized) | 442.80 | 12.30 |
| Polyethylene glycol 3350 | 666.00 | 18.50 |
| SUM | 3600.00 | 100.00 |
| Formulation F | | |
| Active ingredient | 500.00 | 13.89 |
| Flavor | 720.00 | 20.00 |
| Sucrose | 288.00 | 8.00 |
| Corn starch (filler) | 569.20 | 15.81 |
| Sodium lauryl sulfate | 72.00 | 2.00 |
| Sodium pamoate | 72.00 | 2.00 |
| Magnesium stearate | 27.00 | 0.75 |
| Aspartame | 9.00 | 0.25 |
| Glycerol | 234.00 | 6.50 |
| Soybean oil (0.1% BHT-stabilized) | 442.80 | 12.30 |
| Polyethylene glycol 3350 | 666.00 | 18.50 |
| SUM | 3600.00 | 100.00 |

The mixture was formed into individual chunks using a Formax F6™ molding machine and the processing was without any problems like stopping of the movable parts.

Soft chews according to the invention were prepared comprising the following alternative isoxazoline compounds Compound B

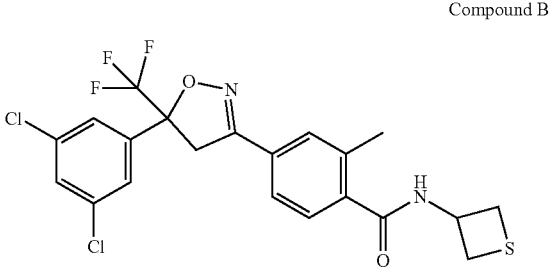

(Isoxazoline)

Compound C

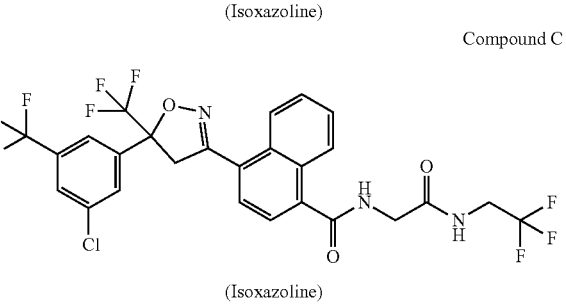

(Isoxazoline)

Compound D

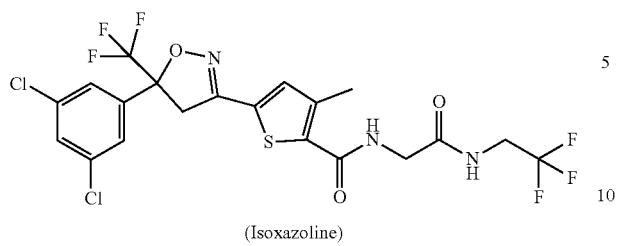

(Isoxazoline)

TABLE 3

Test formulations

| Excipient | 13-009 | 13-010 | 13-011 | 13-012 | 13-013 | 13-014 |
|---|---|---|---|---|---|---|
| Compound B | 13.64% | 4.27% | | | | |
| Compound C | | | 13.64% | 4.27% | | |
| Compound D | | | | | 13.64% | 4.27% |
| 2-pyrrolidone | | 10.19% | | 10.19% | | 10.19% |
| microcrystalline cellulose | | 24.27% | | 24.27% | | 24.27% |
| sodium starch glycolate | | 4.95% | | 4.95% | | 4.95% |
| flavor | 20.0% | 14.56% | 20.0% | 14.56% | 20.0% | 14.56% |
| sucrose | 7.0% | | 7.0% | | 7.0% | |
| corn starch | 16.06% | | 16.06% | | 16.06% | |
| sodium lauryl sulfate | 2.0% | 3.4% | 2.0% | 3.4% | 2.0% | 3.4% |
| sodium pamoate | 2.0% | 2.43% | 2.0% | 2.43% | 2.0% | 2.43% |
| magnesium stearate | 0.75% | 0.49% | 0.75% | 0.49% | 0.75% | 0.49% |
| aspartame | 0.25% | 0.49% | 0.25% | 0.49% | 0.25% | 0.49% |
| glycerin | 7.5% | 2.91% | 7.5% | 2.91% | 7.5% | 2.91% |
| soybean oil | 12.3% | 16.75% | 12.3% | 16.75% | 12.3% | 16.75% |
| PEG 3350 | 18.5% | | 18.5% | | 18.5% | |
| PEG 8000 | | 15.29% | | 15.29% | | 15.29% |

Example 2

Comparative Example Soft Chew

Examples of soft chews that do not contain pamoic acid or salts or esters thereof are set forth below.

| Substance | mass [mg] | % | Result |
|---|---|---|---|
| Formulation G | | | |
| Active ingredient | 500 | 8.93 | Forming machine stops while in process. The |
| Flavor | 1120 | 20 | addition of 2% w/w soybean oil did not result |
| Aspartame | 28 | 0.5 | in a proper process. The addition of further 2% w/w |
| Sucrose | 392 | 7 | soybean oil and 2.5% w/w magnesium |
| Corn starch (filler) | 634 | 11.32 | stearate did not improve the process. |
| Magnesium stearate | 42 | 0.75 | |
| Sodium lauryl sulfate | 112 | 2 | |
| Lactose monohydrate | 560 | 10 | |
| Soybean oil (BHT-stabilized) | 896 | 16 | |
| Glycerol | 420 | 7.5 | |
| Polyethylene glycol 3350 | 896 | 16 | |
| SUM | 5600 | 100 | |
| Formulation H | | | |
| Active ingredient | 502.01 | 8.93 | Forming machine stops during process. After |
| Flavor | 1120.00 | 20.00 | addition of 1% w/w Sodium pamoate machine |
| Sucrose | 1008.00 | 18.00 | stops again. After addition of Sodium pamoate |
| Corn starch (filler) | 575.99 | 10.32 | to reach a final amount of 1.5% w/w the |

-continued

| Substance | mass [mg] | % | Result |
|---|---|---|---|
| Sodium lauryl sulfate | 112.00 | 2.00 | process runs properly. |
| Magnesium stearate | 42.00 | 0.75 | |
| Aspartame | 28.00 | 0.50 | |
| Glycerol | 420.00 | 7.50 | |
| Soybean oil (0.1% BHT-stabilized) | 896.00 | 16.00 | |
| Polyethylene glycol 3350 | 896.00 | 16.00 | |
| SUM | 5600.00 | 100.00 | |
| Formulation I | | | |
| Active ingredient | 200.00 | 6.25 | |
| 2-Pyrrolidone | 294.40 | 9.20 | |
| Microcrystalline cellulose | 769.60 | 24.05 | |
| Colloid Silicon dioxide | 64.00 | 2.00 | |
| Micronized poloxamer 407 (Lutrol Micro 127) | 160.00 | 5.00 | |
| Sodium lauryl sulfate | 160.00 | 5.00 | |
| Flavor | 480.00 | 15.00 | |
| Sodium pamoate | 0.00 | 0.00 | |
| Aspartame | 16.00 | 0.50 | |
| Magnesium stearate | 32.00 | 1.00 | |
| Labrasol | 64.00 | 2.00 | |
| Soy bean oil (0.1% BHT-stabilized) | 464.00 | 14.50 | |
| Polyethylene glycol 8000 | 496.00 | 15.50 | |
| SUM | 3200.00 | 100.00 | |

The initial formulation containing no sodium pamoate is not processable. After addition of 2.5% sodium pamoate the forming process runs properly.

Example 4

Efficacy Against Brown Dog Ticks (*R. sanguineus*) on Dogs

A composition according to the invention with the following excipients was prepared.

| Excipient | Composition (% w/w) |
|---|---|
| Fluralaner-Compound A | 4.27% |
| 2-pyrrolidone | 10.19% |
| microcrystalline cellulose | 24.27% |
| sodium starch glycolate | 4.95% |
| flavor | 14.56% |
| sodium lauryl sulfate | 3.40% |
| sodium pamoate | 2.43% |
| aspartame | 0.49% |
| magnesium stearate | 0.49% |
| glycerol | 2.91% |
| soybean oil | 16.75% |
| Polyethylene Glycol 8000 | 15.29% |

Dogs were randomly assigned to 4 treatment groups of 8 animals each, and one untreated control group of 8 animals. The dogs in the treatment groups were treated with the composition as described above on Day Zero as shown in Table 6:

TABLE 6

| Treatment Groups | |
|---|---|
| Group | Treatment |
| A | Untreated control |
| B | 4.27% fluralaner chewable tablet 8 mg/kg bw |

TABLE 6-continued

| Treatment Groups | |
|---|---|
| Group | Treatment |
| C | 4.27% fluralaner chewable tablet 10 mg/kg bw |
| D | 4.27% fluralaner chewable tablet 12 mg/kg bw |
| E | 4.27% fluralaner chewable tablet 20 mg/kg bw |

The dogs were infested on Day −2 with approximately 50 adult unfed ticks (*R. sanguineus*) and on Day 28 and 56. Ticks were counted approximately 48 h post infestation and on Days 30 and 58 (approximately 48 hour after each post-treatment re-infestation) to evaluate the acaricidal activity in the treated groups.

Table 7 shows the observed tick counts:

TABLE 7

| Brown Dog Ticks (*R. sanguineus*) on dogs-Tick counts - | | | |
|---|---|---|---|
| Group | Day 2 | Day 30 | Day 58 |
| A | 21.25 | 23 | 25.9 |
| B | 0 | 0 | 0 |
| C | 0.125 | 0 | 0 |
| D | 0 | 0 | 1.13 |
| E | 0 | 0 | 0 |

What is claimed is:

1. A soft chewable veterinary pharmaceutical product comprising as ingredients,
sodium pamoate,
one or more active pharmaceutical ingredient,
a liquid component, and
a forming agent;

wherein the amount of sodium pamoate is between 1.5 and 30% w/w.

2. The product according to claim 1 wherein the amount of sodium pamoate is between 2 and 5% w/w.

3. The product according to claim 1, additionally comprising one or more of the following excipients:
a filler,
a stabilizer component,
a flavoring component, and
a sugar component.

4. The product according to claim 1 wherein the active pharmaceutical ingredient is an isoxazoline compound of Formula (I)

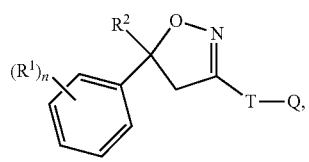

Formula (I)

wherein
$R^1$=halogen, $CF_3$, $OCF_3$, CN,
n=integer from 0 to 3,
$R^2$=$C_1$-$C_3$-haloalkyl,
T=5- or 6-membered ring, which is optionally substituted by one or more radicals Y,
Y=methyl, halomethyl, halogen, CN, $NO_2$, $NH_2$—C=S, or two adjacent radicals Y form together a chain;
Q=X—$NR^3R^4$ or a 5-membered N-heteroaryl ring, which is optionally substituted by one or more radicals;
X=$CH_2$, CH($CH_3$), CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

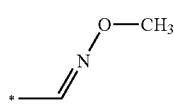 R³-1

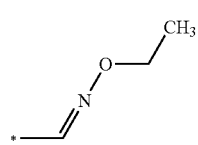 R³-2

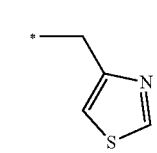 R³-3

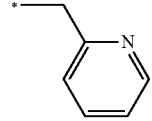 R³-4

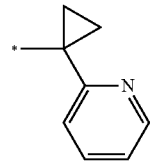 R³-5

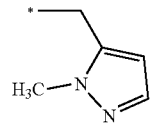 R³-6

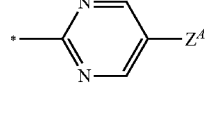 R³-7

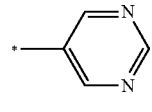 R³-8

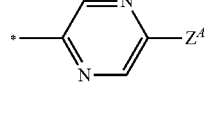 R³-9

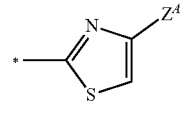 R³-10

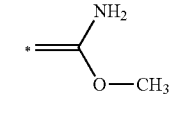 R³-11

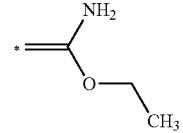 R³-12

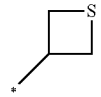 R³-13

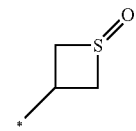 R³-14

-continued

R³-15

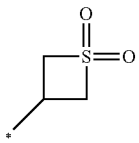

wherein Z⁴=hydrogen, halogen, cyano, halomethyl (CF₃);
R⁴=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;
Or R³ and R⁴ together form a substituent selected from the group consisting of:

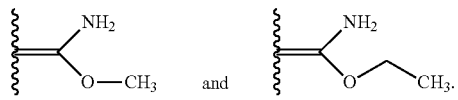

or a salt or solvate thereof.

5. The product according to claim 4 wherein the active pharmaceutical ingredient is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide.

6. The product according to claim 4 wherein the active pharmaceutical ingredient is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

7. The product according to claim 4 wherein the active pharmaceutical ingredient is 4-[5-(3,5-dichlorophenyl)-5-(trifluoromethyl)-4H-isoxazol-3-yl]-2-methyl-N-(thietan-3-yl)benzamide.

8. The product according to claim 4 wherein the active pharmaceutical ingredient is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide.

9. The product according to claim 1 wherein more than one active pharmaceutical ingredient is present.

10. The product according to claim 9 wherein the combination of active pharmaceutical ingredients comprises one or more antiparasitics.

11. The product of claim 1, further comprising one or more excipients.

12. The product of claim 1, wherein the active pharmaceutical ingredient is 4-[5-(3,5-dichlorophenyl)-4,5-dihydro-5-(trifluoromethyl)-3-isoxazolyl]-N—[(Z)-(methoxyimino)methyl]-2-methyl-benzamide.

13. The product of claim 4, wherein n is an integer 1, 2 or 3.

14. The product of claim 4, wherein R² is CF₃ or CF₂Cl.

15. The product of claim 4, wherein two adjacent radicals Y form together a three or four member chain.

16. The product of claim 5, wherein the isoxazoline compound is an enantiomer of 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide.

17. A chewable veterinary pharmaceutical product comprising as ingredients, 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide;
sodium pamoate;
a liquid component comprising one or more oils, one or more non-aqueous solvents and one or more humectants; and
a forming agent;
wherein the amount of sodium pamoate is between 1.5 and 30% w/w.

18. The product according to claim 17 comprising soy bean oil, glycerol and polyethylene glycol 3350.

19. A process for the manufacture of a product according to claim 1 in a forming machine comprising the steps of
a) mixing the ingredients into a dough,
b) filling a mold with dough, and
c) removing the dough from the mold,
wherein in the mixing step a) the sodium pamoate is mixed with the other ingredients;
wherein the amount of sodium pamoate is between 1.5 and 30% w/w.

20. The process of claim 19, wherein the lubricity of a product is increased when filling the mold with dough or when removing the dough from the mold or both.

21. A method of controlling a parasitic insect, acarid or nematode infestation of an animal comprising administering to the animal a soft chewable veterinary pharmaceutical composition comprising
4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide;
sodium pamoate,
a liquid component, and
a forming agent;
wherein the amount of sodium pamoate is between 1.5 and 30% w/w.

22. The method according to claim 21, wherein the liquid component comprises one or more oils, one or more non-aqueous solvents and one or more humectants.

23. The method according to claim 22, wherein the humectant is glycerol.

24. The method according to claim 22, wherein the oil is soybean oil.

25. The method according to claim 21, wherein the forming agent comprises a polyethylene glycol.

26. The method according to claim 21, wherein in the composition comprises soy bean oil, glycerol and polyethylene glycol 3350.

* * * * *